United States Patent [19]
Whitley

[11] Patent Number: 6,004,282
[45] Date of Patent: Dec. 21, 1999

[54] LEG LIFTER APPARATUS

[76] Inventor: Ray D. Whitley, P.O. Box 38, Fruitland, Id. 83619

[21] Appl. No.: 09/070,159

[22] Filed: Apr. 30, 1998

Related U.S. Application Data

[60] Provisional application No. 60/048,219, May 30, 1997.

[51] Int. Cl.$^6$ ................................. A61F 5/00; A61F 5/37
[52] U.S. Cl. .................................. 602/5; 602/23; 128/882
[58] Field of Search ................................. 602/1, 3–5, 23, 602/27, 32–36, 60–62; 128/882

[56] References Cited

U.S. PATENT DOCUMENTS

| | | |
|---|---|---|
| 2,607,340 | 8/1952 | Anderson . |
| 3,153,411 | 10/1964 | Unks ........................................ 602/33 |
| 3,739,772 | 6/1973 | Ennis . |
| 4,019,503 | 4/1977 | Smith . |
| 4,111,195 | 9/1978 | Neufeld . |
| 4,169,468 | 10/1979 | Murphy . |
| 4,495,941 | 1/1985 | Rathvon et al. . |
| 5,014,692 | 5/1991 | Rhoades ................................. 602/23 |
| 5,236,333 | 8/1993 | Barba, Jr. . |
| 5,256,119 | 10/1993 | Tudor ........................................ 482/74 |
| 5,263,916 | 11/1993 | Bobich ................................. 482/74 X |
| 5,291,904 | 3/1994 | Walker ................................. 602/23 X |

Primary Examiner—Richard J. Apley
Assistant Examiner—Denise Pothier

[57] ABSTRACT

A leg lifter apparatus includes a foot connection assembly for connecting to a person's foot region, a first and second leg connection assembly for connecting to a person's first and second leg region, respectively, and a flexible pull line which is connected to the foot connection assembly and which is in sliding contact with the first and the second leg connection assembly. The foot connection assembly includes a first adjustable foot strap and a first rigid foot fixture attached to the first adjustable foot strap. The first rigid foot fixture includes a rigid eye, and the pull line includes a loop connected to the rigid eye. The first leg connection assembly includes a first adjustable leg strap and a first rigid leg fixture attached to the first adjustable leg strap. The second leg connection assembly includes a second adjustable leg strap. The pull line includes a handle portion.

3 Claims, 3 Drawing Sheets

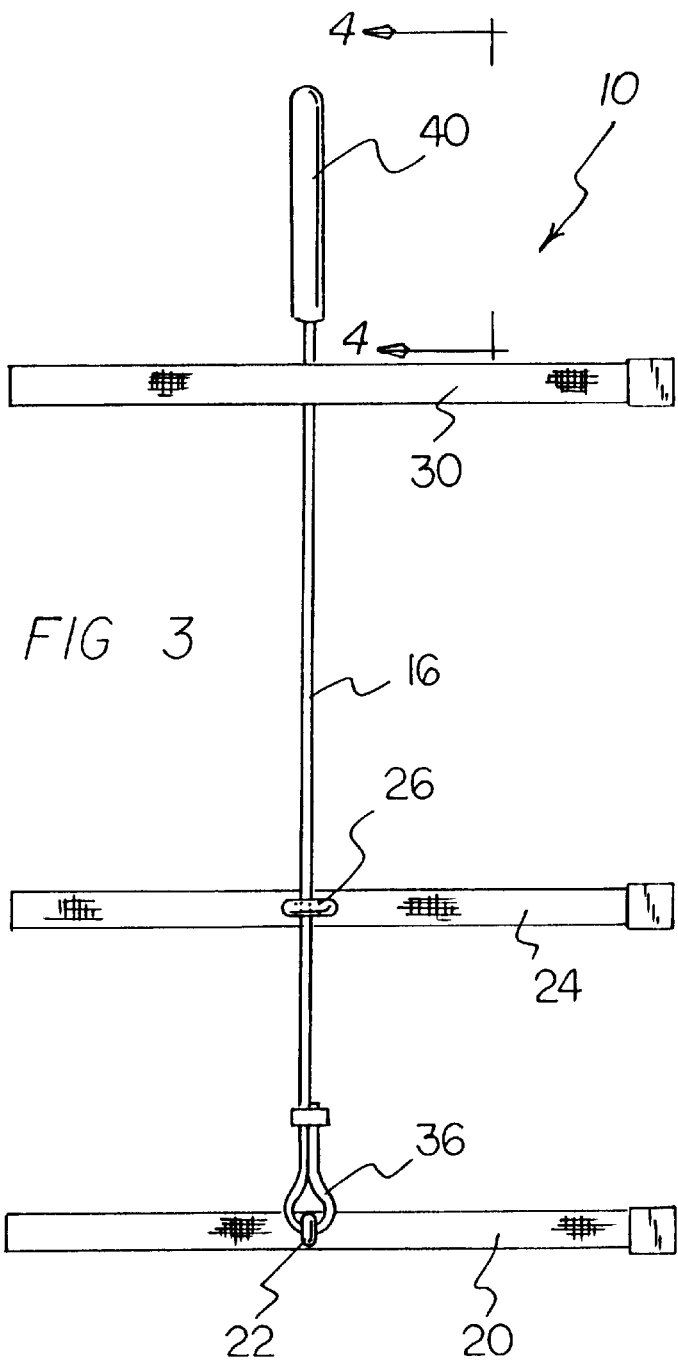
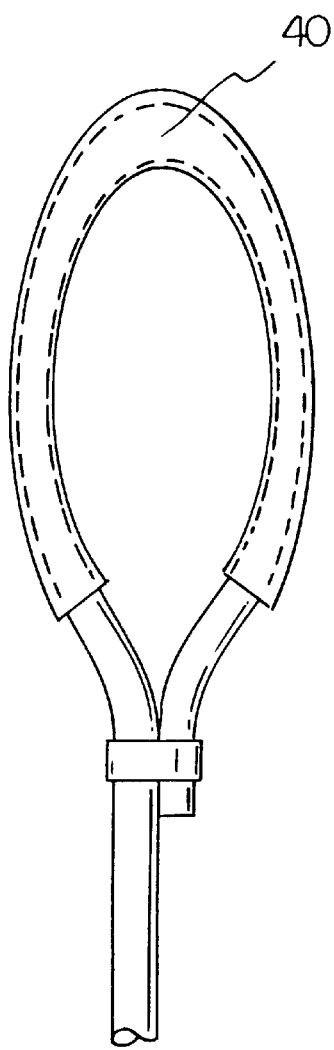

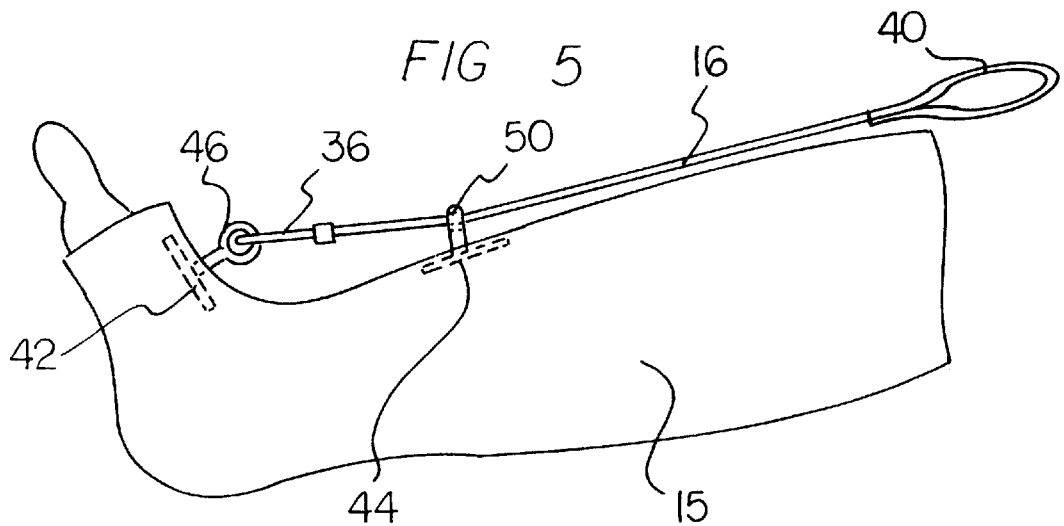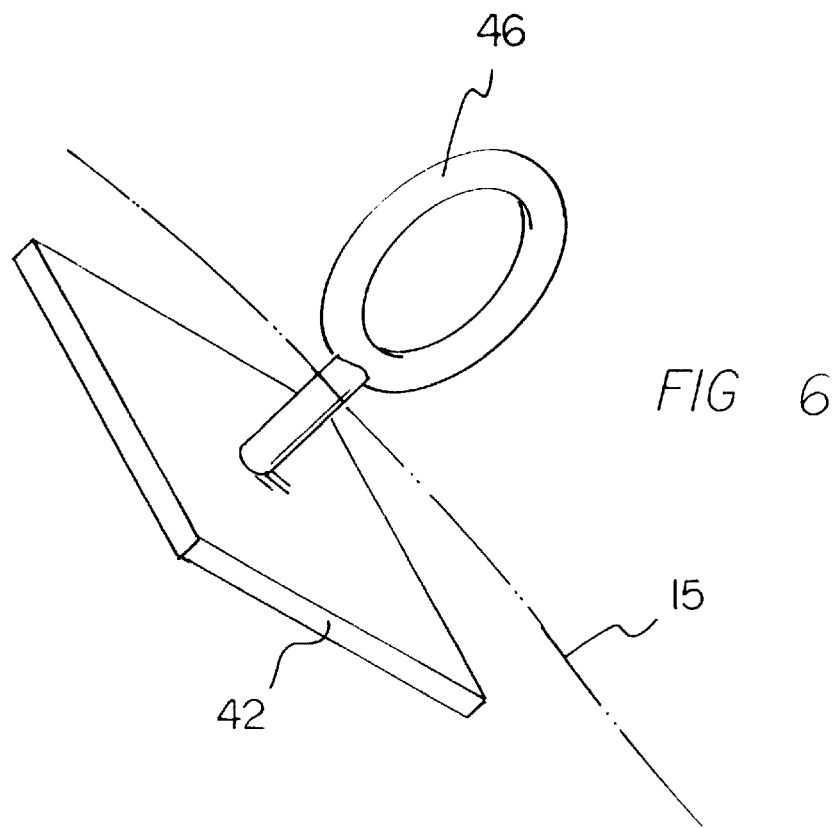

LEG LIFTER APPARATUS

CROSS-REFERENCE TO RELATED APPLICATION

This application claims priority based upon my copending Provisional Application Ser. No. 60/048,219, filed May 30, 1997.

BACKGROUND OF THE INVENTION

1. Field of the Invention

The present invention relates generally to devices for lifting legs in casts and, more particularly, to leg lifter device especially adapted for a cast wearer to lift one's own cast-laden leg.

2. Description of the Prior Art

When a person wears a cast on one's leg, it is often difficult for the person to lift one's cast-laden leg using one's leg alone. Throughout the years, a number of innovations have been developed relating to devices which enable a person to lift one's cast-laden leg, and the following U.S. patents are representative of some of those innovations: Nos. 4,019,503 and 4,495,941. More specifically, U.S. Pat. No. 4,019,503 discloses a cradle assembly that includes an entirely rigid lifting structure for lifting a cast-laden leg. Such an entirely rigid lifting structure tightly restricts the distance between a person's hand and the cast. Also, such a rigid structure tightly limits the range of motion of the hand of a person lifting one's leg. In this respect, it would be desirable if a leg lifter device were provided which does not employ and entirely rigid lifting member.

U.S. Pat. No. 4,495,941 discloses a cast moving device which has a flexible pull line and which has straps attached to only leg portions of the cast. No foot connection assembly is provided with this device. Yet, it is contemplated that lifting a cast would be facilitated if a foot connection assembly were provided on either a foot or foot-covering portion of a cast.

Still other features would be desirable in a leg lifter apparatus. With respect to U.S. Patent Nos. 4,019,503 and 4,495,941 discussed above, it is noticed that straps are provided that fit around the circumference of a cast. Rather than being concerned about straps that may loosen or shift out of position on the cast, it would be desirable if a leg lifter device were provided that included a portion that is implanted in a fixed position in the cast itself.

In addition, the following U.S. patents may be of interest for their disclosure of some additional innovations relating to the lifting of leg casts: Nos. 3,739,772, 4,111,195, 4,169,468, and 5,236,333. More specifically, U.S. Pat. No. 3,739,772 discloses a device that includes a portion which fits over a wearer's shoulder. U.S. Pat. Nos. 4,111,195 and 4,169,468 relate to devices employed for suspending a cast-laden leg from an overhead support. U.S. Pat. No. 5,236,333 discloses an entirely rigid device for lifting a person's leg which, conceivably, could include a cast.

Thus, while the foregoing body of prior art indicates it to be well known to use leg lifter devices, the prior art described above does not teach or suggest a leg lifter apparatus which has the following combination of desirable features: (1) does not employ an entirely rigid lifting member; (2) provides a foot connection assembly for either a foot or foot-covering portion of a cast; and (3) includes a portion that is implanted in a fixed position in the cast. The foregoing desired characteristics are provided by the unique leg lifter apparatus of the present invention as will be made apparent from the following description thereof. Other advantages of the present invention over the prior art also will be rendered evident.

SUMMARY OF THE INVENTION

To achieve the foregoing and other advantages, the present invention, briefly described, provides a leg lifter apparatus which includes a foot connection assembly for connecting to a person's foot region, a first leg connection assembly for connecting to a person's first leg region, and a flexible pull line which is connected to the foot connection assembly and which is in sliding contact with the first leg connection assembly. The foot region includes a foot region of a cast. The first leg region includes a first leg region of the cast. When the person wears the cast and the leg lifter apparatus, the person can pull on the pull line to lift the leg, a second leg connection assembly is connected to a person's second leg region. The second leg region includes a second leg region of a cast.

The foot connection assembly includes a first adjustable foot strap and a first rigid foot fixture attached to the first adjustable foot strap. The first rigid foot fixture includes a rigid eye, and the pull line includes a loop connected to the rigid eye.

The first leg connection assembly includes a first adjustable leg strap and a first rigid leg fixture attached to the first adjustable leg strap. The first rigid leg fixture includes a U-shaped guide member.

The second leg connection assembly includes a second adjustable leg strap. A portion of the pull line is threaded under the second leg connection assembly. The pull line includes a handle portion.

In accordance with a second embodiment of the invention, the foot connection assembly includes a foot fixation plate embedded in a cast and an eye member connected to the foot fixation plate. The first leg connection assembly includes a leg fixation plate embedded in the cast and an eye member connected to the leg fixation plate.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining at least two preferred embodiments of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved leg lifter apparatus which has all of the advantages of the prior art and none of the disadvantages.

It is another object of the present invention to provide a new and improved leg lifter apparatus which may be easily and efficiently manufactured and marketed.

It is a further object of the present invention to provide a new and improved leg lifter apparatus which is of durable and reliable construction.

An even further object of the present invention is to provide a new and improved leg lifter apparatus which is susceptible of a low cost of manufacture with regard to both materials and labor, and which accordingly is then susceptible of low prices of sale to the consuming public, thereby making such leg lifter apparatus available to the buying public.

Still yet a further object of the present invention is to provide a new and improved leg lifter apparatus which does not employ an entirely rigid lifting member.

Still another object of the present invention is to provide a new and improved leg lifter apparatus that provides a foot connection assembly for either a foot or foot-covering portion of a cast.

Yet another object of the present invention is to provide a new and improved leg lifter apparatus which includes a portion that is implanted in a fixed position in the cast.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawing wherein:

FIG. 3 is an enlarged top view of the embodiment of the leg lifter apparatus of FIG. 2 removed from the leg cast.

FIG. 4 is an enlarged side view of the portion of the embodiment of the invention shown in FIG. 3 taken along line 4—4 thereof.

FIG. 5 is a side view showing a second embodiment of the leg lifter apparatus of the invention in which a portion of the apparatus is integrally included into a leg cast.

FIG. 6 is an enlarged perspective view of a portion of the embodiment of the invention shown in FIG. 5.

DESCRIPTION OF THE PREFERRED EMBODIMENT

Figure 1:
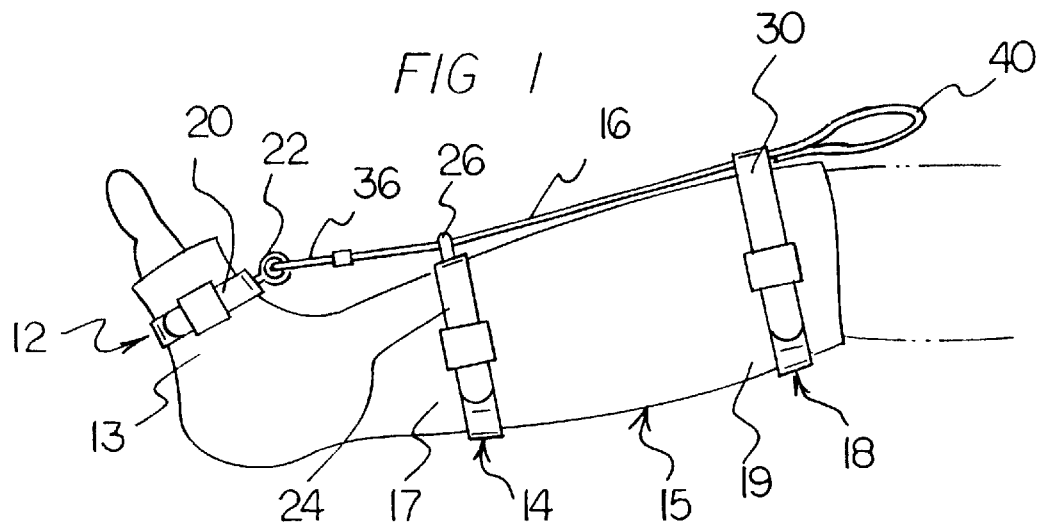
FIG. 1 is a side view showing a first embodiment of the leg lifter apparatus of the invention affixed to the exterior of a leg cast.

With reference to the drawings, a new and improved leg lifter apparatus embodying the principles and concepts of the present invention will be described.

Turning to FIGS. 1–4, there is shown a first embodiment of the leg lifter apparatus which includes a foot connection assembly 12 for connecting to a person's foot region, a first leg connection assembly 14 for connecting to a person's first leg region, and a flexible pull line 16 which is connected to the foot connection assembly 12 and which is in sliding contact with the first leg connection assembly 14. The foot region includes a foot region 13 of a cast 15. The first leg region includes a first leg region 17 of the cast 15. When the person wears the cast 15 and the leg lifter apparatus 10, the person can pull on the pull line 16 to lift the leg. A second leg connection assembly 18 is connected to a person's second leg region. The second leg region includes a second leg region 19 of a cast 15.

The foot connection assembly 12 includes a first adjustable foot strap 20 and a first rigid foot fixture attached to the first adjustable foot strap 20. The first rigid foot fixture includes a rigid eye 22, and the pull line 16 includes a loop 36 connected to the rigid eye 22.

The first leg connection assembly 14 includes a first adjustable leg strap 24 and a first rigid leg fixture attached to the first adjustable leg strap 24. The first rigid leg fixture includes a U-shaped guide member 26.

The second leg connection assembly 18 includes a second adjustable leg strap 30. A portion of the pull line 16 is threaded under the second leg connection assembly 18. The pull line 16 includes a handle portion 40.

In broadest concept, the leg lifter apparatus 10 can be used on a person's leg that does not bear a cast. In this respect, foot connection assembly 12 is attached to a foot region of the person, the first leg connection assembly 14 is attached to a first leg region of the person, and the second leg connection assembly 18 is attached to a second leg region of the person.

Figure 2:
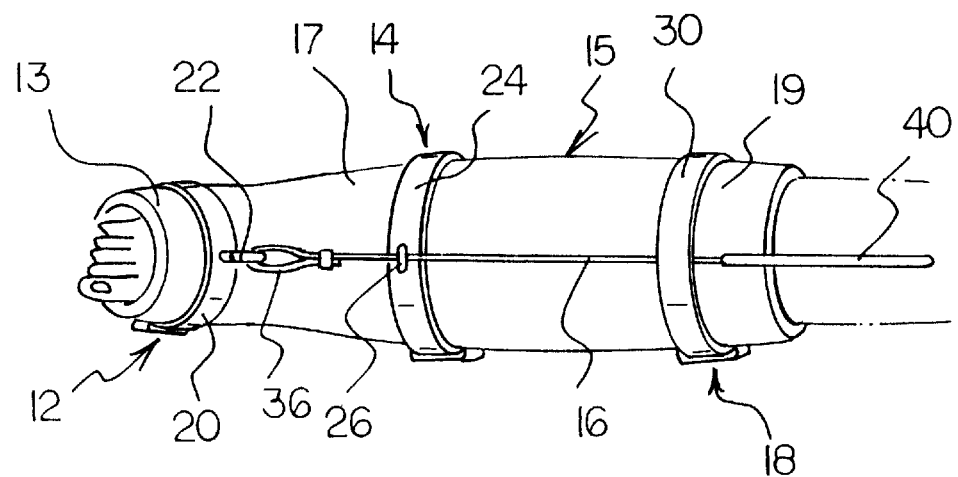
FIG. 2 is a top view of the embodiment of the leg lifter apparatus shown in FIG. 1.

In other circumstances, the leg lifter apparatus 10 is used with a person's leg which bears a cast 15, such as shown in FIGS. 1 and 2. In this mode of use, the foot connection assembly 12 is attached to the foot region 13 of the cast 15, the first leg connection assembly 14 is attached to the first leg region 17 of the cast 15, and the second leg connection assembly 18 is attached to the second leg region 19 of the cast 15.

As shown in FIGS. 1 and 2, the loop 36 of the pull line 16 is connected to the rigid eye 22 of the foot connection assembly 12. A portion of the pull line 16 is threaded through the U-shaped guide member 26 of the first leg connection assembly 14. A portion of the pull line 16 is passed under the second adjustable leg strap 30 on top of the cast 15. For the person to lift one's leg, the person pulls on the handle portion 40 of the pull line 16. The pulling force is transmitted through the pull line 16 to the rigid eye 22, through the first adjustable foot strap 20, and to the foot region 13 of the cast 15. This causes the foot region 13 of the cast 15 to be lifted. When this is done, the leg is pivoted upwards around the person's hip. If he person moves the handle portion 40 in a transverse direction as the leg is lifted, the leg can be swung in a lateral direction. To lower the leg, the person gradually reduces the pulling force on the pull line 16.

Turning to FIGS. 5–6, a second embodiment of the invention is shown. Reference numerals are shown that correspond to like reference numerals that designate like elements shown in the other figures. In addition, the foot connection assembly 12 includes a foot fixation plate 42 embedded in a cast 15 and an eye member 46 is connected to the foot fixation plate 42. The first leg connection assembly 14 includes a leg fixation plate 44 embedded in the cast 15 and an eye member 50 is connected to the leg fixation plate 44.

To install the second embodiment of the invention, a cast is partially made. Then, the foot fixation plate 42 and the leg fixation plate 44 are placed on the partially made cast. Then, the fabrication of the cast is completed so that the foot fixation plate 42 and the leg fixation plate 44 are embedded in the finished cast 15. In using the second embodiment of the invention, the second embodiment of the invention is used substantially in the same way as the first embodiment of the invention.

The components of the leg lifter apparatus of the invention can be made from inexpensive and durable metal, plastic, and cordage materials.

As to the manner of usage and operation of the instant invention, the same is apparent from the above disclosure, and accordingly, no further discussion relative to the manner of usage and operation need be provided.

It is apparent from the above that the present invention accomplishes all of the objects set forth by providing a new and improved leg lifter apparatus that is low in cost, relatively simple in design and operation, and which may advantageously be used without employing an entirely rigid lifting member. With the invention, a leg lifter apparatus provides a foot connection assembly for either a foot or foot-covering portion of a cast. With the invention, a leg lifter apparatus is provided which includes a portion that is implanted in a fixed position in the cast.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

Hence, the proper scope of the present invention should be determined only by the broadest interpretation of the appended claims so as to encompass all such modifications as well as all relationships equivalent to those illustrated in the drawings and described in the specification.

Finally, it will be appreciated that the purpose of the annexed Abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

What is claimed as being new and desired to be protected by Letters Patent of the United States is as follows:

1. A method of lifting a person's leg, comprising the steps of:

attaching a foot connection assembly to a foot of the person, attaching a first leg connection assembly to a first leg portion of the leg, attaching a flexible pull line to the foot connection assembly, such that the flexible pull line is in sliding engagement with the a first leg connection assembly, and pulling on the flexible pull line such that the person's foot and leg are lifted by the foot connection assembly and the first leg connection assembly, further including the steps of:

attaching a second leg connection assembly to a second leg portion of the leg, placing the flexible pull line in sliding contact with the second leg connection assembly, and pulling on the flexible pull line such that the person's foot and leg are lifted by the foot connection assembly, the first leg connection assembly, and the second leg connection assembly.

2. A leg lifter assembly for use on the foot region, proximal leg region and distal leg region of a person, said apparatus comprising in combination:

a first connection assembly for connecting to a person's foot region, said first connection assembly comprising a first adjustable, circumferentially extending strap, a second connection assembly for connecting to a person's proximal leg region, said second connection assembly comprising a second adjustable, circumferentially extending strap, and a third connection assembly for connecting connected to a person's distal leg region, said third connection assembly comprising a third adjustable, circumferentially extending strap, a flexible pull line having first and second opposed ends adapted to be connected to the first foot connection assembly and further adapted to be in sliding contact with said first leg connection assembly and said second leg connection assembly, first connection means on said first adjustable, circumferentially extending strap for connecting said flexible line to said first adjustable, circumferentially extending strap, said first connection means comprising a rigid eye, said first end of said flexible pull line being connected to said rigid eye, and second connection means on said second adjustable, circumferentially extending strap for slidably connecting said flexible line to said second adjustable, circumferentially extending strap, said second connection means comprising a U-shaped rigid guide member, said second end of said flexible pull line adapted to be passed through said U-shaped rigid guide member, whereby said first connection assembly is adapted to be circumferentially fitted about the foot region of a person, said second connection assembly is adapted to be fitted about the proximal leg region of a person and said third connection assembly is adapted to be circumferentially fitted about the distal leg region of a person with said flexible pull line extending from said rigid eye on said first connection assembly through said U-shaped rigid guide member on said second connection assembly and between said third connection assembly and said person's distal leg region sufficiently to enable said person to grasp said second end of said flexible pull line.

3. The apparatus of claim 2 wherein the pull line includes a handle portion.

* * * * *